US 12,255,036 B2

United States Patent
Rachlin

(10) Patent No.: US 12,255,036 B2
(45) Date of Patent: Mar. 18, 2025

(54) INCONTINENCE DETECTION DEVICE

(71) Applicant: Mad Bladder, Inc., Tucson, AZ (US)

(72) Inventor: Daniel Joseph Rachlin, San Jose, CA (US)

(73) Assignee: MAD BLADDER, INC., Tucson, AZ (US)

( * ) Notice: Subject to any disclaimer, the term of this patent is extended or adjusted under 35 U.S.C. 154(b) by 0 days.

(21) Appl. No.: 18/066,898

(22) Filed: Dec. 15, 2022

(65) Prior Publication Data

US 2023/0187162 A1 Jun. 15, 2023

Related U.S. Application Data

(60) Provisional application No. 63/289,680, filed on Dec. 15, 2021.

(51) Int. Cl.
*H01J 11/12* (2012.01)
*H01J 11/22* (2012.01)

(52) U.S. Cl.
CPC .............. *H01J 11/12* (2013.01); *H01J 11/22* (2013.01)

(58) Field of Classification Search
CPC ..... H01J 11/12; H01J 11/22; A61F 2013/424; A61F 13/42
See application file for complete search history.

(56) References Cited

U.S. PATENT DOCUMENTS

| 7,241,933 B2 | 7/2007 | Shapira | |
|---|---|---|---|
| 2019/0110730 A1 | 4/2019 | Pop et al. | |
| 2019/0167489 A1* | 6/2019 | Hellmold | G01N 33/00 |
| 2019/0167490 A1* | 6/2019 | Hellmold | A61F 13/15699 |
| 2019/0240078 A1 | 8/2019 | Li et al. | |
| 2021/0205150 A1 | 7/2021 | Mehta et al. | |

FOREIGN PATENT DOCUMENTS

| EP | 3451988 A1 * | 3/2019 | ......... A61B 5/0002 |
|---|---|---|---|
| EP | 3451988 B1 | 3/2019 | |

\* cited by examiner

*Primary Examiner* — David D Davis
(74) *Attorney, Agent, or Firm* — NGUYEN TARBET IP LAW

(57) ABSTRACT

Most current incontinence detection systems are expensive, difficult to use, uncomfortable to wear, or suffer limitations in the scope of detected events. However, the present invention features an incontinence detection system that uses inexpensive technologies and is disposable. The system can indicate the degree and persistence of wetness. The degree of wetness can be measured across various factors, including geometrical coverage via multiple independent detection points, each comprising a "detection cell." A suitably networked system can determine the time and location of wetness. Each cell might be tuned for various factors such as material fluid affinity and exposure area. An advantage of the invention is the ease with which it can be adapted to distinguish fecal incontinence as distinct from urinary incontinence; both forms of incontinence can be monitored using the same system described herein. Another advantage includes the ability to estimate urine salinity.

5 Claims, 5 Drawing Sheets

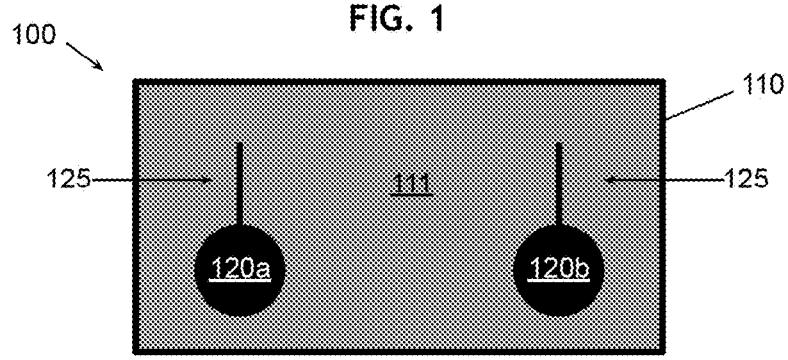
FIG. 1
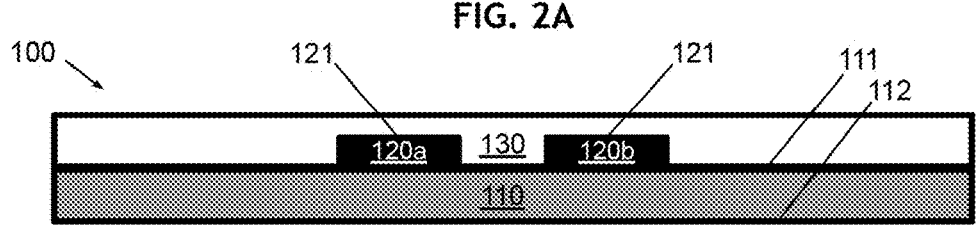
FIG. 2A
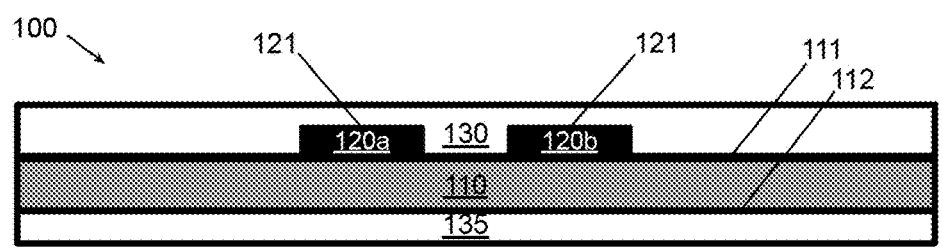
FIG. 2B
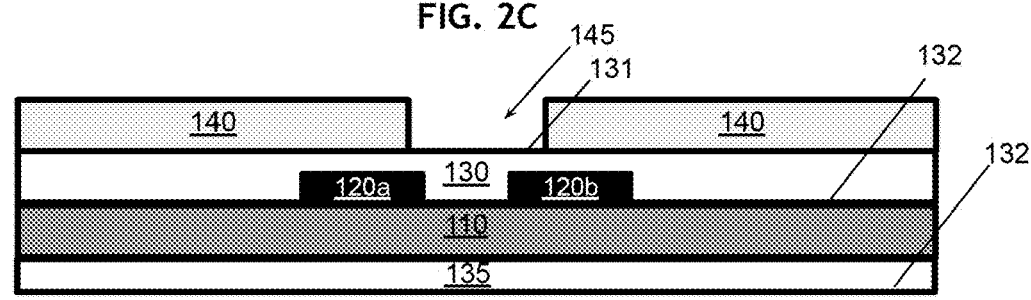
FIG. 2C
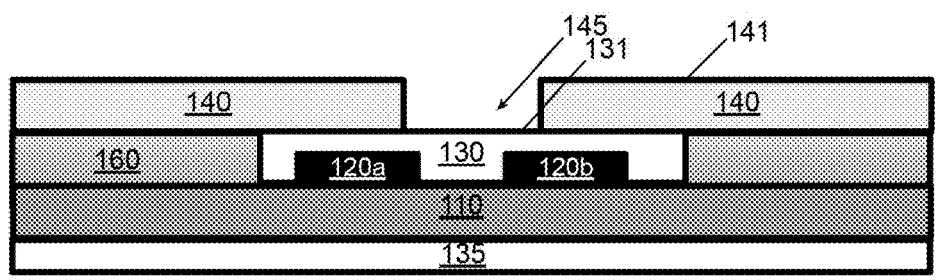

INCONTINENCE DETECTION DEVICE

CROSS-REFERENCES TO RELATED APPLICATIONS

This application is a non-provisional and claims benefit of U.S. Provisional Application No. 63/289,680 filed Dec. 15, 2021, the specification of which is incorporated herein in their entirety by reference.

FIELD OF THE INVENTION

The present invention provides systems for detection of urinary and fecal incontinence.

BACKGROUND OF THE INVENTION

Fluid detecting systems are abundant in the art, prominent amongst them being the use of electronics to detect conductivity between wetted electrodes. Many commercial products are available based on these simple electrical principles, including those to detect bedwetting by children. In addition, some optical approaches have been disclosed, presenting added challenges in design, manufacturing, and cost.

Fluid absorbent pads are commonly available to manage incontinence. Washable pads typically present with a fibrous fill that absorbs fluid through a large wettable surface area offered by a fiber matrix. Non-reusable pads are commonly made of a fluid-absorbing matrix such as hydrogels, often expanding when attaining full fluid capacity.

Electrical approaches for incontinent event detection have the advantage of design simplicity and low cost. A typical architecture incorporates a disposable component attached to a reusable controller. The disposable component provides at least one electrode pair that, when bridged by fluid, becomes capable of conducting electric current. The controller interrogates the electrode pair, yielding a measure of circuit conductivity. However, the present state of the art limits the utility of this approach. Measuring the conductivity level resulting from wetting the medium, often clothing, that connects a pair of electrodes can easily be performed using well-known and inexpensive approaches. Unfortunately, measuring the degree of conductivity poorly translates into the degree of wetness and misses other important information. One reason for this is that urine salinity, which strongly affects conductivity, is highly variable.

A further unmet need is the detection of fecal incontinence based upon electrical approaches and that selectively respond to properties unique to stool vis-à-vis urine. Optical approaches have also been suggested. However, they are less proven and are prone to cost challenges.

The present invention remedies many of the limitations of the current state of the art. The systems and methods described herein can acquire a rich array of monitoring data from a disposable element (e.g., a pad-strip), providing a real-time measure of the degree of incontinence, the distinction of type—urinary vs. fecal, and an estimate of urine salinity. The design centers on measuring the exposure of the pad-strip to urine or feces, and can be designed with minimal performance dependence upon the underlying method of fluid management including diapers or incontinence absorbance pads. Furthermore, the disposable element is amenable to inexpensive, high volume manufacturing approaches such as converter or roll-to-roll processing.

BRIEF SUMMARY OF THE INVENTION

It is an objective of the present invention to provide systems that allow for the detection of fecal and urinary incontinence, as specified in the independent claims. Embodiments of the invention are given in the dependent claims. Embodiments of the present invention can be freely combined with each other if they are not mutually exclusive.

The present invention features a wearable disposable sensor pad that, in conjunction with a wearable controller device, yields key measurements pertaining to incontinence. The sensor pad may comprise a long strip that fits in a diaper (see FIG. 4 or FIG. 7). The systems may comprise multiple discrete urine sensing cells, each contain fluid absorbing wicks with ohmic connections to electrical pads, allowing the conductivity of the wicks to be continuously measured by the attached controller. The stream of sensor information is transmitted wirelessly from each controller worn by a facility resident, home resident, or other wearer to at least one base station (not shown) which in turn transmits the data to servers that forward information to caregiver endpoints consisting of workstations or mobile apps, portions of which are represented in the figure.

In some embodiments, the present invention features an incontinence detection cell. The incontinence detection cell may comprise a substrate comprising a first surface and a second surface, a first absorbable material layer disposed on the first surface of the substrate, and at least one pair of electrodes disposed between the first surface of the substrate and the first absorbable material layer. In some embodiments, incontinence is detected when the pair of electrodes is bridged by a connecting material (e.g., a conducting material; e.g., urine or fecal matter), the pair of electrodes become operably connected and a closed circuit is formed. In some embodiments the incontinence detection cell further comprises a barrier. The barrier may uncouple the pair of electrodes from the first absorbable material layer.

In other embodiments, the present invention features an incontinence detection system comprising one or more incontinence detection cells as described herein, and a controller operably coupled to the electrodes of the one or more incontinence detection cells. The incontinence detection system may comprise a substrate comprising a first surface and a second surface, a first absorbable material layer disposed on the first surface of the substrate, at least one pair of electrodes disposed between the first surface of the substrate and the first absorbable material layer, and a barrier uncoupling at least one of the pairs of electrodes from the first absorbable material layer. In some embodiments, incontinence is detected when the pair of electrodes is bridged by a connecting material (e.g., urine or fecal matter), the pair of electrodes become operably connected and a closed circuit is formed.

One of the unique and inventive technical features of the present invention is the use of pairs of electrodes and an absorbable material layer with or without barriers. Without wishing to limit the invention to any theory or mechanism, it is believed that the technical feature of the present invention advantageously provides for the detection of urinary and fecal incontinence events. None of the presently known prior references or work has the unique inventive technical feature of the present invention.

Any feature or combination of features described herein are included within the scope of the present invention provided that the features included in any such combination are not mutually inconsistent as will be apparent from the context, this specification, and the knowledge of one of ordinary skills in the art. Additional advantages and aspects of the present invention are apparent in the following detailed description and claims.

BRIEF DESCRIPTION OF THE SEVERAL VIEWS OF THE DRAWING(S)

The features and advantages of the present invention will become apparent from a consideration of the following detailed description presented in connection with the accompanying drawings in which:

FIG. 1 depicts two electrodes printed on a substrate.

FIGS. 2A, 2B, 2C, 2D, and 2E shows a cross-sections of various embodiments of incontinence detection cells (e.g., urinary incontinence detection cells) described herein.

FIGS. 3A, 3B, and 3C shows a cross-sections of various embodiments of incontinence detection cells (e.g., fecal incontinence detection cells) described herein.

DETAILED DESCRIPTION OF THE INVENTION

Figure 2D:
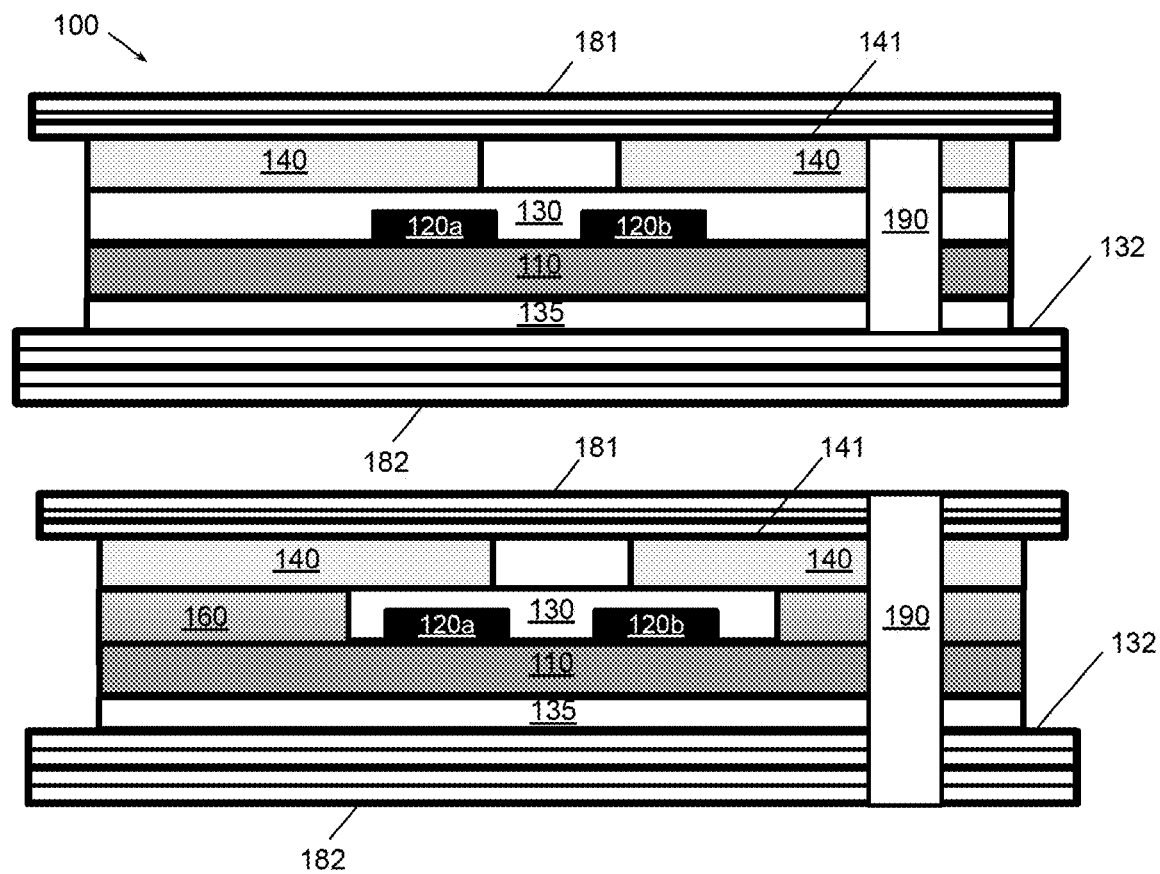

Following is a list of elements corresponding to a particular element referred to herein:

100 Incontinence Detection Cell
110 Substrate
111 First Surface
112 Second Surface
120 Electrode
121 First Surface
125 Conductive Lead
126 Electrical Contact
130 First Absorbable Material
131 First Surface
132 Second Surface
135 Second Absorbable Material
140 Insulating Film
141 First Surface
145 Gaps
150 Barrier
151 Aperture
152 Non-Permeable Layer
155 Air Barrier
160 Controller
165 Connector
170 Absorbing Matrix
175 Saturation Layer
181 First Permeable Layer
182 Second Permeable Layer
190 Drainage Channel Referring now to FIGS. 1-7, the present invention features incontinence detection cells and systems for detecting both urinary and fecal incontinence.

As used herein, a "detection cell" or an "incontinence detection cell" may be used interchangeably and refer to single electrical units for detection of urinary or fecal incontinence.

Referring to FIG. 1, the present invention may feature a pair of electrodes (120a and 120b) comprising exposed conductor pads disposed on a first surface (111) of a substrate (110). Each of the electrodes may further comprise a conductive lead (125a, 125b). The conductive leads (125a and 125b) may be disposed on the first surface (111) of a substrate (110). In some embodiments, the conductive leads (125a and 125b) may be printed circuit traces and may allow for electrical contact (126) with the pair of electrodes (120a and 120b).

In some embodiments, the electrodes (120) comprises silver, coppers, carbon, gold, or a combination thereof. Additionally, any two-dimensional conductive material may be used in accordance with the electrodes (120) of the present invention.

In some embodiments, the electrodes (120) may comprise common materials used on etched printed circuit comprising copper, silver, and/or gold. In other embodiments, the electrodes (120) may comprise conductive inks comprising metal powder (e.g., silver) and carbon.

In some embodiments, the substrate (110) comprises a non-conductive substrate. In some embodiments, the non-conductive substrate comprises a flexible film, including but not limited to polyimide or polyester. In some embodiments, the substrate (110; e.g., the non-conductive substrate) comprises paper. In some embodiments, the substrate (110) is non-conductive. In some embodiments, the substrate (110) is insulating. Moreover, any other suitable polymers may be used in accordance with the substrates (110) described herein.

In some embodiments, the conductive leads (125a and 125b) may comprise copper, silver, or carbon. In other embodiments, the conductive leads (125a and 125b) may comprise wires. The technology described herein may incorporate etching or printing approaches. The traces (i.e., conductive leads (125a and 125b)) typically require insulation, which usually prompts adding a cover layer film. A circuit can comprise a simple "single layer" as it pertains to the conductive portion (e.g., the electrodes (120) and the conductive leads (125)), the conductive material adhering to a bottom non-conductive layer (i.e., substrate (110)).

In some embodiments, the conductive leads (125a and 125b) are insulated (e.g., with an insulating layer (140), e.g., a cover lay) and routed to a controller (160) that can interrogate the electrical conductivity between the electrodes (120a, 120b) using a test voltage (or current). In some embodiments, the insulating layer (140), e.g., the cover lay, may prevent fluid from contacting the conductive elements (e.g., the conductive leads (125)) beneath.

The present invention features an incontinence detection cell (100; see FIG. 2A). The incontinence detection cell (100) may comprise a substrate (110) comprising a first surface (111) and a second surface (112), a first absorbable material layer (130) disposed on the first surface (111) of the substrate (110), and at least one pair of electrodes (120a, 120b) disposed between the first surface (111) of the substrate (110) and the first absorbable material layer (130). In some embodiments, incontinence is detected when the pair of electrodes (120a, 120b) is bridged by a connecting material (e.g., urine or fecal matter), the pair of electrodes (120a, 120b) become operably connected and a closed circuit is formed.

In some embodiments, the first absorbable material layer (130) is configured to connect the pair of electrodes (120a, 120b). In some embodiments, e.g., in an urinary detection cell, the first absorbable material layer (130) is disposed on a surface (121) of the electrodes. In some embodiments, when the first absorbable material layer (130) is dry, an open circuit is formed between the pair of electrodes (120a, 120b), and when the first absorbable material layer (130) is wetted, the connecting material comprises the wet first absorbable material layer (130), thus operably connecting the pair of electrodes (120a, 120b) and forming the closed circuit between the pair of electrodes (120a, 120b) for detecting incontinence. In some embodiments, when the first absorbable material layer (130) is dry an open circuit is formed between the pair of electrodes (120a, 120b) and when the first absorbable material layer (130) is wetted (e.g., with urine) a closed circuit is formed between the pair of electrodes (120a, 120b) and incontinence is detected.

In some embodiments, the incontinence detection cell (100) comprises a second absorbable material layer (135) disposed on the second surface (112) of the substrate (110) (See FIG. 2B). In some embodiments, the first absorbable material layer (130) and second absorbable material layer (135) comprises polyester with dabbed amounts of polyethylene or other thermoplastics.

In some embodiments, the first absorbable material layer (130) and/or second absorbable material layer (135) may be heat bonded. In other embodiments, the first absorbable material layer (130) and second absorbable material layer (135) may act as both a wettable substrate and a permeable layer. Without wishing to limit the present invention to any theory or mechanism it is believed that with the first and second absorbable material layer (130,135) act as both a wettable substrate and a permeable layer, the absorbable material layers have excellent properties for providing a dry feel, while having some storage of fluid to persist the signal.

In some embodiments, the first absorbable material layer (130) and the second absorbable material layer (135) may be used to sandwich the substrate (110; e.g., a flex circuit), such that the substrate (110) is disposed between the first absorbable material layer (130) and the second absorbable material layer (135).

In some embodiments, the first absorbable material layer (130) may be a thin temperature stable polyester that is partially or slowly wettable, such that a fluid can wick away slowly through pores. In some embodiments, the first absorbable material layer (130) may be attachable via heat bonding by way of thermoplastic domains. Heat bonding is a general approach to fusing all layers together described herein, although this does not preclude use of curing adhesives.

Additional embodiments of the incontinence detection cells described herein are shown in FIG. 2C, 2D and FIGS. 3A, 3B, and 3C. Referring to FIGS. 2A, 2B, 2C and 2D, a cross-section view from the side of the present invention is shown.

Referring to FIG. 2C, the incontinence detection cell (100) comprises a substrate (110) comprising a first surface (111) and a second surface (112), a first absorbable material layer (130) disposed on the first surface (111) of the substrate (110), at least one pair of electrodes (120a, 120b) disposed between the first surface (111) of the substrate (110) and an insulating film (140) disposed on a first surface (131) of the first absorbable material layer (130). In some embodiments, the first absorbable material layer (130) is disposed on a first surface (121) of the electrodes and on the first surface (111) of the substrate (110) and the second absorbable material (135) is disposed on the second surface (112) of the substrate (110).

In some embodiments, the electrodes (120a, 120b) may be visible on the second surface (112) of the substrate (110).

In some embodiments, the insulating film (140) comprises an insulating polymer e.g., polyethylene. In other embodiments, the insulating film (140) comprises paper treated to be waterproof. In some embodiments, the insulating film (140) may further comprise a plurality of gaps (145) within the insulating film (140). In some embodiments, the plurality of gaps (145) are configured to allow a liquid to reach the first absorbable material layer (130).

In some embodiments, the first absorbable material layer (130) is configured to extend the length of the substrate (110; see FIG. 2C, top). In other embodiments, the first absorbable material layer (130) is configured to extend only between a pair of electrodes (120a, 120b; see FIG. 2C, bottom). In the abovementioned embodiment, the system (100) may further comprise an adhesive layer (160) disposed between the first surface (111) of the substrate (110) and the insulating film (140). In some embodiments, the adhesive layer (160) comprises a low melting point polymer (e.g., for heat bonding). In some embodiments, the adhesive layer (160) comprises polyurethane.

In some embodiments, the first absorbable material layer (130) is configured to connect the pair of electrodes (120a, 120b). In some embodiments, when the first absorbable material layer (130) is dry there is no conductive bridge between the electrodes (120a, 120b); however when the first absorbable material layer (130) is exposed to a fluid (e.g., urine) a conductive bridge is formed. Without wishing to limit the present invention to any theories or mechanisms, it is believed that fluid may be drawn into the first absorbable material layer (130) by wicking or capillary action.

In some embodiments, the first absorbable material layer (130) may be doped with a compound such as salt which substantially increases the conductivity of the fluid. Without wishing to limit the present invention to any theory or mechanism it is believed that doping the first absorbable mater layer (130) may be useful to guarantee high conductivity even if the fluid (e.g., urine) itself has very low ionic concentration. Additionally, doping may be used when a strong "binary" signal (e.g., high conduction or none) is required.

In some embodiments, the first absorbable material layer (130) may be in direct contact or connected through a wick with the second absorbable material layer (135), such that when the first absorbable material layer (130) is wetted the wetness may drain (e.g., slowly) into the second absorbable material layer (130). This allows the wetness of the first absorbable material layer (130) to wicked away, and thus may also allow the signal from the electrodes (120) to dissipate. Without wishing to limit the present invention to any theory or mechanism it is believed that the aforementioned mechanism (i.e., the first absorbable material layer (130) in direct contact with the second absorbable material layer (135)) may allow for distinguishing between persistent wetness events and separate wetness events. In some embodiments, the first absorbable material layer (130) may be in connected to the second absorbable material layer (135) by other means to allow fluid to pass from the first absorbable material layer (130) to the second absorbable material layer (135).

In some embodiments, the first absorbable material layer (130) and the second absorbable material layer (135) may comprise different shapes. For example, the second absorbable material layer (135) may have various geometric relationships to the first absorbable material layer (130).

Referring now to FIG. 2D the incontinence detection cell (100) described herein may further comprise a first permeable layer (181) disposed on a first surface (141) of the insulating layer (140), and/or a second permeable layer (182) disposed on a second surface (132) of the second absorbable material layer (130). In some embodiments, the first permeable layer (181) may be attached to the substrate (110). In other embodiments, the first permeable layer (181) may be attached on the perimeter of the substrate (110).

In some embodiments, the first and second permeable layer (181, 182) may comprise polyester. In other embodiments, the first and second permeable layer (181, 182) may comprise nylon mesh, paper, fabrics designed for wicking that can be made of cotton or other materials.

The first permeable layer (181) may be designed to provide a measure of comfort, and may comprise fabric or other clothing-mimicking material. In some embodiments, the first permeable layer (181) may be non or poorly wettable while retaining its permeability to fluid. Such materials include but are not limited to those commonly used for non-disposable incontinence pads, where they serve to provide a permeable top layer with drainage into a large reservoir of absorbent material such as hydrogel or fluid-holding fabric. In some embodiments, the bottom layer (e.g., the second absorbable material layer (135) or the second permeable (182) may be disposed on a diaper, an absorbent pad, or an undergarment.

In some embodiments, the second permeable layer (182) and/or the second absorbable material layer (135) may ensure fluid is wicked consistently from other (e.g., overlying) structures. In some embodiments, the second permeable layer (182) and/or the second absorbable material layer (135) may rest on the diaper which can grab the fluid.

In some embodiments, the first absorbable material layer (130) and/or the second absorbable material layer (135) may allow for fast diffusion of a liquid through the thickness of the material (e.g., diffusion of a liquid from the first surface (131) to the second surface (132)) and slow diffusion of a liquid laterally. In some embodiments, the first and second permeable layer (181, 182) may allow for fast diffusion of a liquid through the thickness of the material and slow diffusion of a liquid laterally.

In some embodiments, lateral wicking may be slow through an absorbable or permeable layer, serving interests of the design such as continuity of absorbable layer over multiple electrode pairs. In other cases, lateral wicking may be fast, requiring steps such as physical discontinuities or impermeable barriers between absorbable layer associated with each cell.

In some embodiments, the incontinence detection cells (100) described herein may further comprise one or more drainage channels (190). The drainage channels (190) may allow flow of fluid from top to bottom—either to facilitate migration of fluid into the bottom layer or beyond into the surrounding environment. In some embodiments, the drainage channels (190) may be disposed through the substrate (110) and the first absorbable material layer (130). In some embodiments, the drainage channels (190) may be disposed through the substrate (100), the first and second absorbable material layer (130, 135), and the insulating film (140; see FIG. 2D, top). In other embodiments, the drainage channels (190) may be disposed through the entire incontinence detection cell (100), such as to form a hole through the cell (see FIG. 2D, bottom). In some embodiments, the drainage channels (190) may be terminated at the second absorbing material layer (135).

Without wishing to limit the present invention to any theories or mechanisms, it is believed that drainage capability, especially on a first surface (101; i.e., top surface) of cells (100) described herein is important to prevent accumulation of fluid which may contact a user/wearer, as prolonged skin contact with urine may result in significant health risks. In some embodiments, the cells (100) described herein may be placed upon an underlying absorbent structure (e.g., a diaper) such that fluid may drain through the drainage channels (190) and/or around the cell (100) itself. In other embodiments, the cell (100) may further comprise or be within a matrix of absorbent material. Therefore, these embodiments not only allow for detection of incontinence, but it also serves to mitigate them directly.

The ability to determine overflow or saturation is covered below. We note here that the absorbent reservoir may be on the top side or bottom side. It may be designed to allow overflow fluid toward the bottom. This might be the case where both top and bottom are equipped with absorbent structures, where it is necessary for drainage from the top to bottom side of the pad-strip.

Alternatively, the pad-strip may require some pass-through of fluid to reach past the bottom-most surface of the device. This will be the case especially if the pad-strip sits is positioned upon an absorbent structure as might be provided by a diaper or absorbent pad.

The upward direction in FIG. 2 is toward the body and will be denoted as the upper or top side. The opposite lower or bottom side might typically rest on wearable fabric such as an undergarment or diaper. The pad-strip may extend for several inches and be attached to the controller (160) in a way that achieves electrical coupling between pad-strip and controller (160). Electrical coupling is achieved through direct contact of mating conductive surfaces. In the case of alternating current (AC) signals, coupling may not require direct contact between conductors—there being other options such as capacitive or inductive coupling. Capacitive coupling has advantages in that the controller (160) can have its contacts buried under a durable insulating and perhaps molded substrate, thus protecting the contacts, and preventing potential direct current (DC) electric current leaks or water ingress.

In some embodiments, the first absorbable material layer (130) may provide a "memory" function. For example, once sufficiently wetted, the first absorbable material layer (130) may retain moisture for a period long enough to ensure detection during polling, but short enough to enable multiple events to spread out over longer periods of time to be distinguished. A controller (160) may monitor or poll the system intermittently (e.g., every 5 to 60 seconds).

In some embodiments, the incontinence detection cells (100) described herein further comprise a controller (160). The controller (160) may comprise a programmable microcontroller The periodic polling can be accomplished by many standard means, including a timer that intermittently "wakes up" a microcontroller used in the controller (160). This device may in turn energize other components such as signal multiplexing switches, amplifiers, and analog to digital (A2C) converters. A2C converters may be built into the microcontroller, the richness of peripherals such as this yielding the term "system on a chip" SOC. By carefully allocating time slots for polling the device, power consumption can be reduced, extending the lifetime of the battery used for the controller (160).

In some embodiments, when the electrodes (120a and 120b) are bridged by air or dry medium, there will be no conductivity. A wetting event, which bridges the electrodes (120a and 120b) with an ionic fluid such as urine, will yield a measurable conductivity.

Figure 3A:
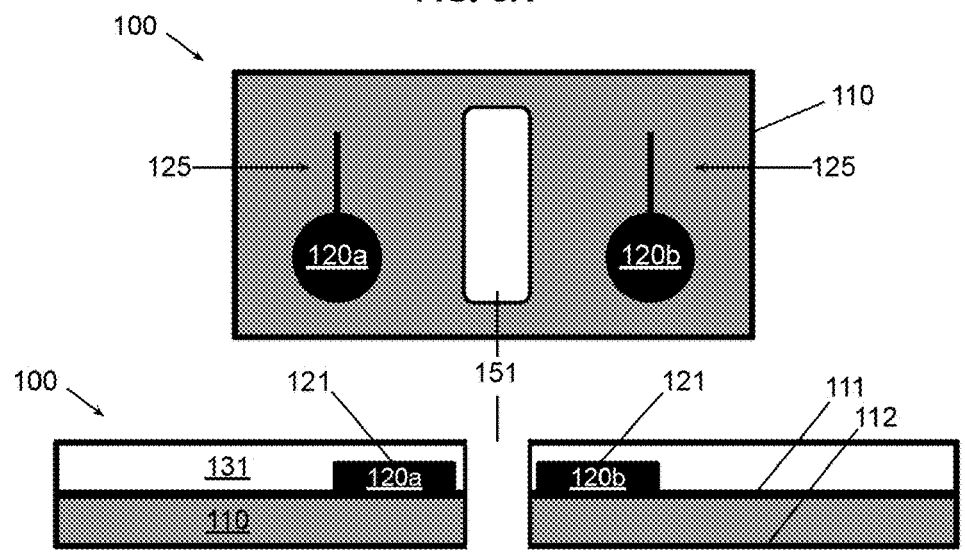
Figure 3B:
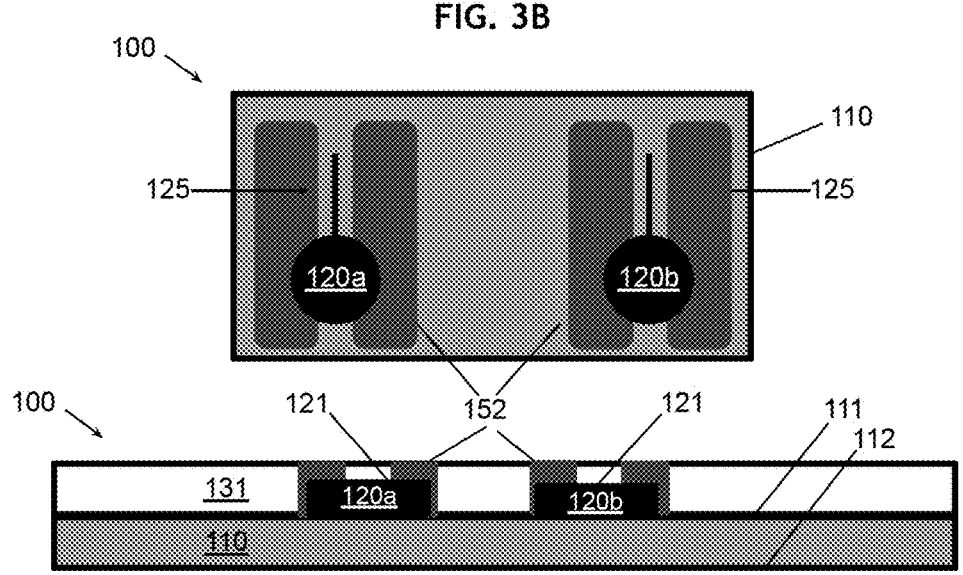
Figure 3C:
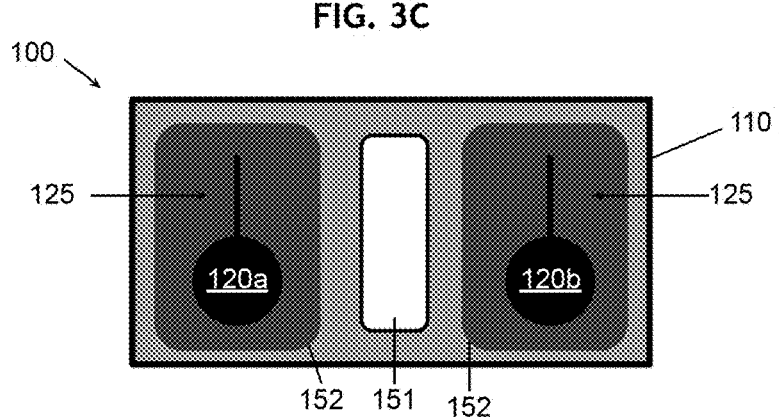

The cells (100) described herein have the additional advantage of detecting fecal incontinence as well as urinary incontinence. The cells (100) to detect fecal incontinence are capable of detecting a persistently wet and semi-solid object that is in contact with a pair of electrodes (120a, 120b). FIGS. 3A, 3B and 3C show non-limiting examples of cells (100) that may be used to detect fecal incontinence. The cell (100) may comprise a pair of electrodes (120a, 120b) disposed on a first surface (111) of a substrate (110), a first absorbable material layer (130) disposed on the first surface (111) of the substrate (110), and a barrier (150). The barrier may uncouple the pair of electrodes (120a, 120b) from the first absorbable material layer (130). In some embodiments, the barrier (150) comprises an aperture (151) disposed through the substrate (110) and the first absorbable material layer (130) (FIG. 3A). In other embodiments, the barrier (150) comprises a non-permeable layer (152) (FIG. 3B). In some embodiments, the barrier (150) comprises a plurality of non-permeable layers (152). In some embodiments, the non-permeable layers (152) may be disposed on a portion of a first surface (121) of an electrode (120). In other embodiments, various infusion techniques as describe herein may be used to make a portion of the first absorbable material layer (130) nonpermeable (e.g., a portion near an electrode (120). In further embodiments, the barrier (150) comprises an aperture (151) and a nonpermeable layer (152) (FIG. 3C).

Without wishing to limit the present invention to any theory or mechanism it is believed that the barriers (150) described herein prevent a fluid (e.g., urine (i.e., a connecting material) from bridging the pair of electrodes (120a, 120b; i.e., operably connecting the electrodes) and forming closed circuit; however, the barrier allows a semi-solid object (e.g., fecal matter (i.e., a connecting material) to operationally connect the electrodes (120a, 120b) to form a closed circuit.

In some embodiments, the connecting material comprises a semi solid object (e.g., fecal matter). In some embodiments, when the connecting material (e.g., a semi solid object; e.g., fecal matter) is absent, an open circuit is formed between the pair of electrodes (120a, 120b), wherein when the connecting material (e.g., a semi solid object; e.g., fecal matter) is present and bridges the pair of electrodes (120a, 120b), the closed circuit is formed between the pair of electrodes (120a, 120b) and incontinence is detected.

In some embodiments, the fecal incontinence detection cells (100) described herein require a wet solid structure (e.g., fecal matter) to form the bridge between the two electrodes (120a, 120b).

In some embodiments, the non-permeable layer (152) may be bare plastic film. In some embodiments, a textile, paper or other similarly composed interface that allows for permeability of liquid may be placed under the aperture (151).

The fecal detection system (100) may further comprise at least one drainage channel (190). In some embodiments, the drainage channel (190) allows for fluids to drain into an absorbing reservoir, such as an underlying diaper, or bulk absorbent layers that may be in the pad-strip itself (e.g., the second absorbable material layer (135) or the second permeable layer (182).

To summarize, the invention embodiments as described so far reference an electrical approach for detection of urinary and fecal incontinence. The two detection cells described in FIGS. 1, 2A, 2B, 2C, 2D, 2E, 3A, 3B, and 3C comprise conceptionally a detection element—in this case electrical in nature. Electrical detection has the advantage of low cost and ease of manufacture. The invention furthermore may comprise other elements such as an absorbable material layer (130) that may be associated with the detection cells (e.g., the urinary detection cells). Combining a pair of electrodes with other associated elements such as an absorbable material layer (130) yields a rich range of possibilities, especially as various properties of the elements can be adjusted.

The present invention may further feature an incontinence detection system (200). In some embodiments, the incontinence detection system (200) comprises at least one urinary incontinence detection cell as described herein. In other embodiments, the incontinence detection system (200) comprises at least one fecal incontinence detection cell as described herein. In some embodiments, the incontinence detection system (200) comprises at least one urinary incontinence detection cell and at least one fecal incontinence detection cell.

In some embodiments, the incontinence detection system (200) comprising one or more incontinence detection cells (100) as described herein, and a controller (160) operably coupled to the electrodes (120) of the one or more incontinence detection cells (100).

The incontinence detection system (200) may comprise a plurality of urinary incontinence detection cells and a plurality fecal incontinence detection cell. In some embodiments, the systems (200) described herein may be disposed on a diaper, an absorbent pad, or an undergarment.

The incontinence detection system (200) may comprise at least one urinary incontinence detection cell and at least one fecal incontinence detection cell. In some embodiments, the urinary incontinence detection cell comprises a substrate (110) comprising a first surface (111) and a second surface (112), at least one pair of electrodes (120a, 120b) disposed on the first surface (111) of the substrate (110), and a first absorbable material layer (130) disposed on a first surface (121) of the electrodes and on the first surface (111) of the substrate (110; see FIG. 2A). In some embodiments, the fecal incontinence detection cell comprises a pair of electrodes (120a, 120b) disposed on a first surface (111) of a substrate (110), a first absorbable material layer (130) disposed on the first surface (111) of the substrate (110), and a barrier (150).

The present invention may feature an incontinence detection system (200) comprising a substrate (110) comprising a first surface (111) and a second surface (112), a first absorbable material layer (130) disposed on the first surface (111) of the substrate (110), at least one pair of electrodes (120a, 120b) disposed between the first surface (111) of the substrate (110) and the first absorbable material layer (130), and a barrier (150) uncoupling at least one of the pairs of electrodes (120a, 120b) from the first absorbable material layer (130). In some embodiments, incontinence is detected when the pair of electrodes (120a, 120b) is bridged by a connecting material, the pair of electrodes (120a, 120b) become operably connected and a closed circuit is formed.

In some embodiments, the first absorbable material layer (130) is disposed on a surface (121) of the electrodes, wherein when the first absorbable material layer (130) is dry, an open circuit is formed between the pair of electrodes (120a, 120b), wherein when the first absorbable material layer (130) is wetted, the connecting material comprises the wet first absorbable material layer (130), thus operably connecting the pair of electrodes (120a, 120b) and forming the closed circuit between the pair of electrodes (120a, 120b) for detecting incontinence.

In some embodiments, the connecting material comprises a semi solid object (e.g., fecal matter), and when the connecting material (e.g., a semi solid object, e.g., fecal matter) is absent, an open circuit is formed between the pair of electrodes (120a, 120b), wherein when the connecting material (e.g., a semi solid object, e.g., fecal matter) is present and bridges the pair of electrodes (120a, 120b), the closed circuit is formed between the pair of electrodes (120a, 120b) and incontinence is detected.

Figure 4:
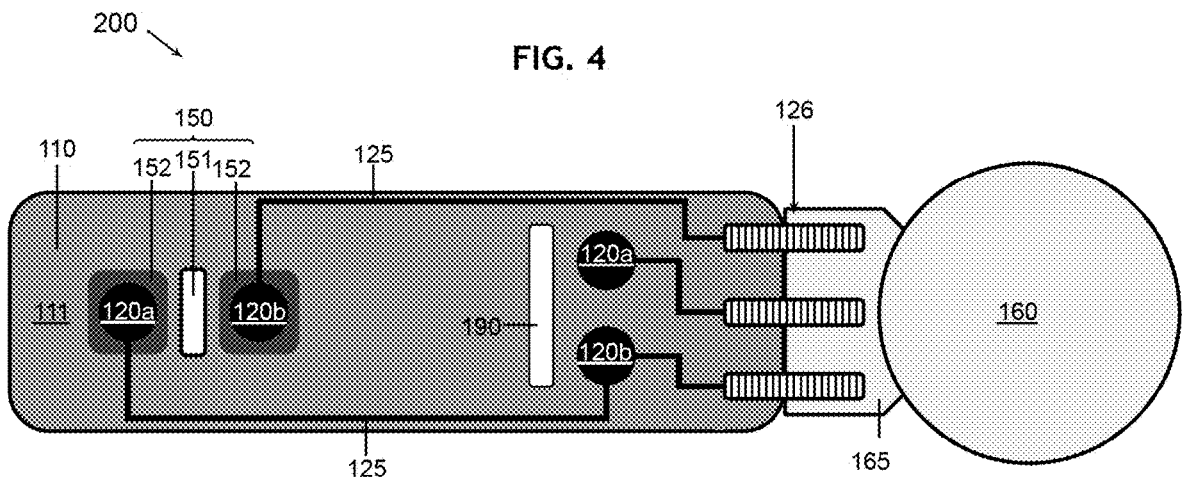
FIG. 4 shows a system level view of the invention.

FIG. 4 depicts a non-limiting simplified example of a incontinence detection system (200) as described herein comprising one urinary incontinence detection cell (100) and one fecal incontinence detection cell (100). The system (200) comprises a substrate (110; e.g., a flexible circuit), two pairs of electrodes (120a, 120b) disposed on a surface (111) of the substrate (110). Each electrode (120) further comprises a conductive lead (121) and electrical contacts (126; e.g., "finger") for making connection via a connector (165) attached to a controller (160). In regard to the fecal incontinence detection cell (100) the pair of electrodes are separated by a barrier (150, e.g., a nonpermeable layer (152) and an aperture (151)). The system (200) may further comprise a drainage channel (190). Not shown are potentially other layers, occupying top (toward viewer) and bottom (away from viewer), that may be present, such as fabric that may provide wicking of fluid away from skin and some degree of fluidic control such as partial impeding or retention of fluid. The means of attaching the flex to the controller (160) are representative of many approaches known in the art.

In some embodiments, the electrical contacts (126; e.g., "fingers") on the substrate (110) are operably connect to corresponding electrical contacts (126) on the controller (160).

While the electrical connection between the system (200) and controller (160) is shown in FIG. 4 as an extension of the substrate (110; e.g., a flex circuit), other approaches may be used, such as a wire bundle, or flex connector attachable to both the flex circuit and the controller (160). Furthermore, electrical contact (126) may be made by opposing mating pairs of electrodes (120a, 120b), whose size and number may be dictated by the need to ensure ease of alignment and full conduction through every contact (126). Generally, a smaller number of electrodes (120) and a larger size thereof will be an advantage. The scope of the present invention is not limited as to a means in making electrical connections with the controller (160).

In some embodiments, the controller (160) comprises a memory, a processor operably coupled to the memory and the electrodes, and a transmitter operably coupled to the processor. In some embodiments, the memory comprises computer-readable instructions that, when executed by the processor, causes the processor to perform operations comprising detecting signals from the electrodes and transmitting said signals to a server via the transmitter.

The shape of the system (200) shown in FIG. 4 may mimic that of many absorbent pads prevalent on the market that are intended to be worn between the legs. The invention observes no limit in overall shape or specific placement. In some embodiments, the controller (160) may be clipped to or made to adhere to an article of clothing such as the edge of an undergarment or diaper. The clip or adhesive element may be separate entities, built into the controller (160) (specifically a clip), or designed into the pad-strip. For example, the system (200) described herein may comprise adhesive backing for specific attachment to the controller (160). The adhesive may be positioned to ensure there is adequate electrical contact (126) between controller (160) and pad-strip. The system (200) may have further adhesive attachments to make attachment of the controller (160) to an article of clothing. In this case, adhesive may be placed on both sides of the flex extension. A clip may still serve as an option to keep the unit stably affixed, perhaps providing needed pressure to ensure electrical contact. Further features may be designed into the controller (160), such as detents, to aid in proper alignment of the flex extension and the controller (160) during attachment.

A single incontinence detection system (200) as described herein may support a plurality of detection cells (100)— wherein they might be interrogated independently or in combination. Furthermore, detection cells (100) may share certain components, such as electrodes (120) or an absorbable material layer (130). For example, 3 electrodes (120) can yield 3 pairwise combinations. A cell structure can be built using each of these pairs. The advantage of this approach is that the number of electrodes (120; e.g., electrical pads), and therefore leads (125) going to the controller (160), can be reduced. The total number of cells that can be created from N electrical pads is $N*(N-1)/2$. For example, 6 electrodes (120) might support up to 15 detection cells (100). With conventional art, utilizing 15 interactions between 6 electrical pads may be of very limited utility. On the other hand, by controlling the properties of each cell, considerable information can be obtained, as described below.

In a system as described above, an electrode (120) connects to a lead that may reversibly connect to a controller (160). In the simplest case, the controller (160) might provide a voltage source and a current detector that is sampled using a channel that can be enabled and allow passage to an analog to digital converter (ADC). Many SOC's contain a built-in ADC peripheral, with multiplexed channels. External analog multiplexers can be connected to enable more channels. While straightforward enough, a limitation comes with making numerous connections between a typically disposable "strip" as exemplified in FIG. 1 and FIG. 2 and a reusable controller (160). There are many standard approaches for connecting flexible printed circuits to a rigid board. A common approach is to use a flexible printed circuit (FPC) cable or flat flexible cable (FFC) extension matched to a receptacle. The robustness of these direct "off-the-shelf" approaches is questionable for a wearable where attachment must be done by a caregiver or consumer. Fewer leads to connect may enhance the robustness of the connection apparatus.

In some embodiments, the system (200) described herein further comprises an undergarment (e.g., a diaper, or an absorbent pad), and the plurality of incontinence detection cells (100) are disposed on the undergarment (e.g., a diaper, or an absorbent pad).

Simultaneous wetness and salinity detection: The signal obtained in a detection cell (100) described herein is detectable based on both degree of wetness (saturation) of the absorbable material layer (130) and ionic concentration. Because conductance is proportional to both degree of wetness and salinity, there is ambiguity. Thus, the present invention provides a system and methods for detecting wetness and salinity.

For example, the present invention may comprise two detection cells (100) close proximity, such that they are wetted to the same extent. Furthermore, the two detection cells (100) may share a connection to another absorbable material, that would tend to equalize the degree of wetness experienced by the first absorbable material (130) of each cell. In some embodiments, at least one of the two detection cells (100) may be impregnated (e.g., the first absorbable material layer (130)) may be impregnated) with a certain concentration of dried salt or other conductivity enhancing material, such that the detection cell (100) becomes a reference cell. The concentration of the conductivity enhancing material may be on the order of a threshold deemed to represent a high value in urine, such as might be caused by dehydration. In some embodiments, for low amounts of wetness and/or low urine salinity, the salt impregnated detection cell (100) will measure far less resistance than the other detection cell (100). On the other hand, for high values of salinity, both detection cells (100) will show similarly very low resistance.

In other embodiments, two absorbable material layers (130) may be fluidly connected or placed in direct contact with one another, one absorbable material layer (130) having a greater affinity than the other absorbable material layer (130). The absorbable material layer (130) with the higher affinity may be exteriorly exposed, so that it may become in contact with a fluid (e.g., urine). In such embodiments, the absorbable material layer (130) with the higher affinity would require a high degree of wetness before the lower affinity absorbable material layer (130) becomes wet. This lower affinity absorbable material layer (130) may be used to bridge two electrodes. The approach is useful in itself—to vary the degree of wettability in a detection cell (100) and to place its absorbable material layer (130) in competition with another.

Figure 5:
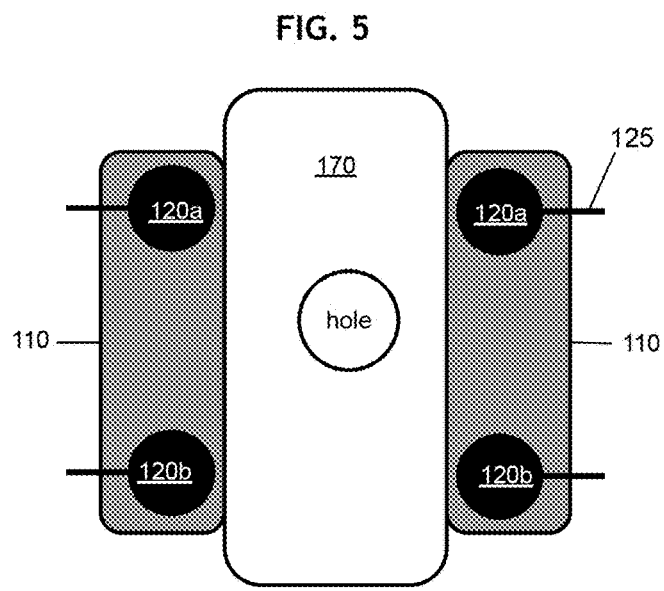
FIGS. 5 and 6 show non-limiting examples of configurations of cells and systems described herein that may detect wetness and salinity.

Measuring the degree of wetness on this basis, in combination with the approach of estimating salinity, can improve the ability of the detection cells (100) and systems (200) described herein to simultaneously estimate wetness and salinity. An example is shown in FIG. 5. Two detection cells (100) as described herein (i.e., comprising a pair of electrodes (120a, 120b) disposed on a substrate (110), and a first absorbable material layer (130) disposed on a first surface (121) of the electrodes and on the first surface (111) of the substrate (110)). When either of the first absorbable material layers (130) a closed circuit is formed between the pair of electrodes (120a, 120b). In association with the absorbable material layer (130) there may be another absorbing matrix (170). In some embodiments, the absorbable material layer (130) of each of the detection cells do not have direct contact with the exterior, and thus cannot be directly wettable externally. On the other hand, the absorbing matrix (170) does have exposure to the exterior, and can, for example, be directly wetted via a urinary event. For example, the absorbing matrix (170) may be exposed through a top hole. Thus, while a significant area is exposed, there is still a requirement that fluid wick through the absorbing matrix (170) before the first absorbable material layer (130) of one of the detection cells is wetted. The affinity of each of these first absorbable material layers (130) may be selected based on the desirable level of wetness sensitivity. Assume that the absorbing matrix (170) equally distributes its wetness, and therefore each detection cell (100) becomes equally wetted. If the detection cells (100) are designed as described earlier with different salinities, a comparison of resistance resulting from the same degree of wetness will indicate relative salinity. It is important that the absorbing matrix (170) be able to come to an equilibrium of uniform fluid distribution.

Figure 6:
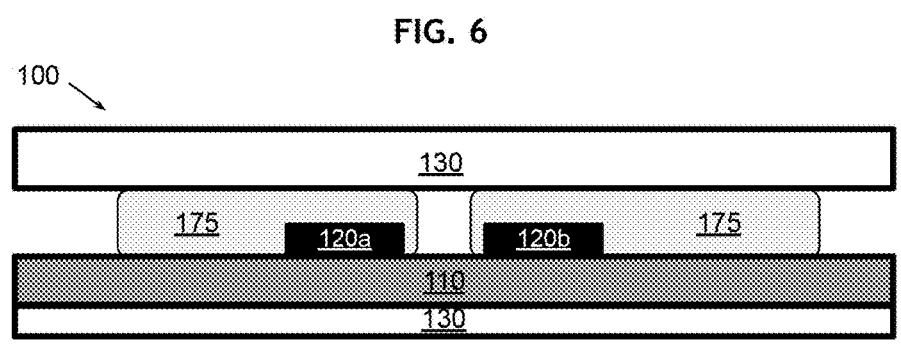
Figure 7:
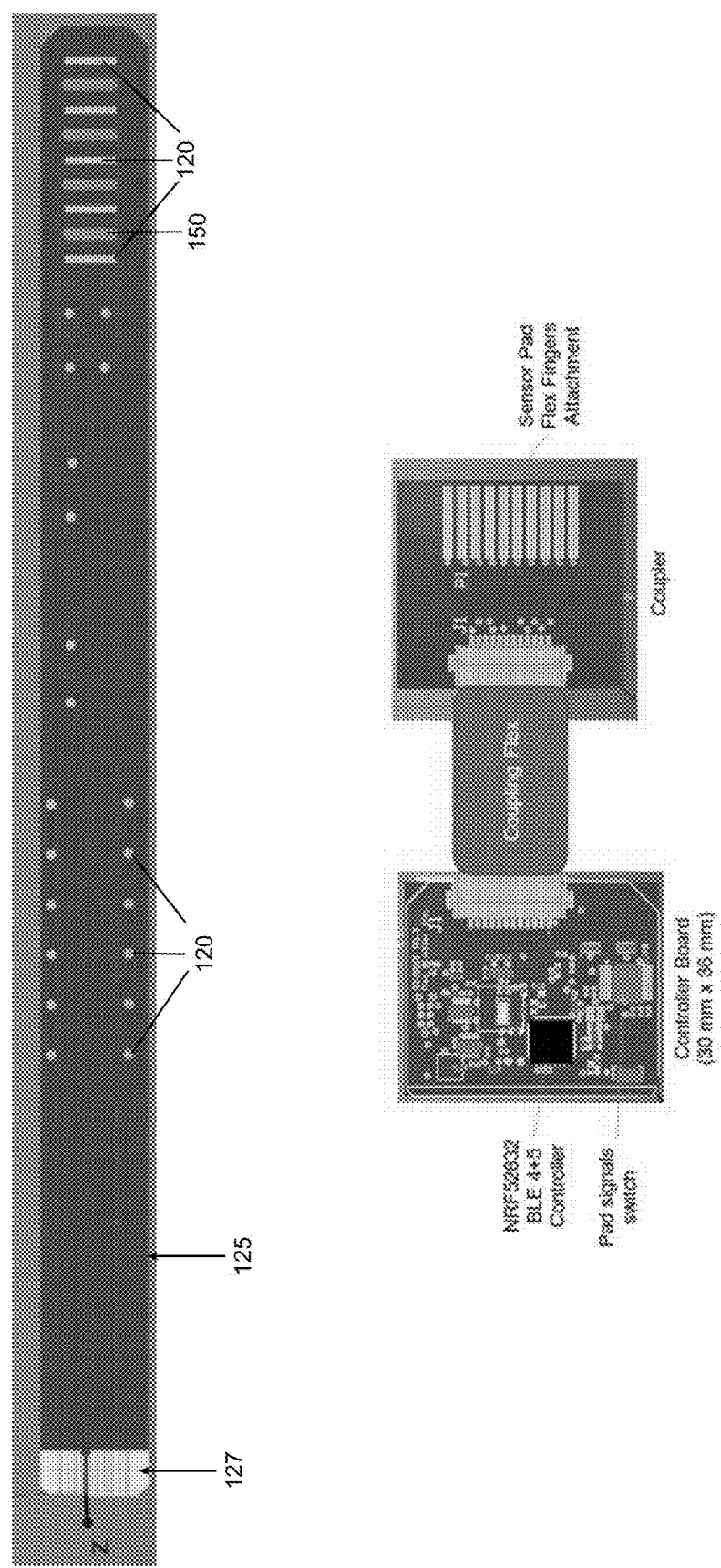
FIG. 7 shows non-limiting example of the systems (top) and a controller (left board) and coupler (right board; bottom) as described herein.

Alternatively, the cells described herein may further comprise an saturation layer (175) disposed between the substrate (100) and the first absorbable material layer (130), see FIG. 6. In some embodiments, the saturation layer (175) must be saturated before a close circuit is created between the pair of electrodes. In some embodiments, the conductivity of the saturation layer (175) is proportional to salinity.

Figure 2E:
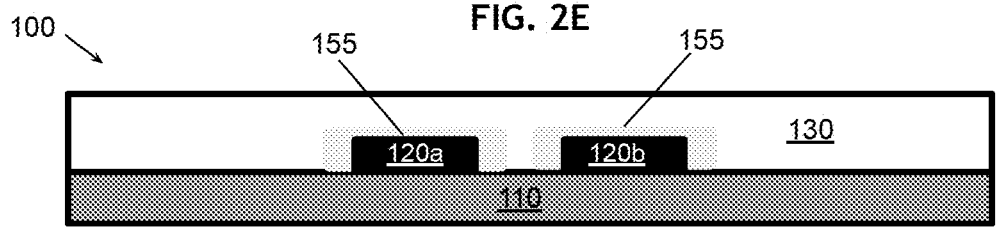

In some embodiments, the aforementioned detection cell further comprises an air barrier (155) between the first absorbable material layer and at least one of the electrodes (120) (see FIG. 2E). A controlled barrier can be formed from mesh or perforated polymer film as examples. The polymer can form a complete layer in the whole structure (easier manufacturing)—between the textile and the printed circuit. It might even be part of the flex circuit (e.g. cover lay) itself.

In some embodiments, the air barrier (155) may separate the first absorbable material layer (130) from the electrode (120). Without wishing to limit the present invention to any theory or mechanism, it is believed that the air barrier (155) allows for conductivity to be proportional to salinity. For example, when the first absorbable material layer (130) is saturated, fluid escaped into air channels of the barrier, completing the circuit. The reverse will tend to happen, as the substrate drains, it will reabsorb the fluid.

In some embodiments, the air barrier (155) may extend laterally across the entire detection cell (100). In other embodiments, the air barrier (155) may be disposed near at least a portion of an electrode (120).

When the water absorbing substrate saturates, fluid enters the gap, and conductivity ensues. Because we know that we are saturated, the conductivity is now directly relatable to the salinity. Thus, when we obtain conductivity, we know it is from a saturated structure (fully known state) and thus conductivity is proportional to salinity. In some embodiments, the detection cell (100) has a binary (yes, no) wetness detection, and when wet, the salinity is linear to conductivity.

As used herein, the term "about" refers to plus or minus 10% of the referenced number.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting essentially of" or "consisting of", and as such the written description requirement for claiming one or more embodiments of the present invention using the phrase "consisting essentially of" or "consisting of" is met.

The reference numbers recited in the below claims are solely for ease of examination of this patent application, and are exemplary, and are not intended in any way to limit the scope of the claims to the particular features having the corresponding reference numbers in the drawings.

What is claimed is:

1. An incontinence detection system (200) comprising:
   a) a substrate (110) comprising a first surface (111) and a second surface (112);
   b) a first incontinence detection cell (100) comprising:
      i) a first absorbable material layer (130) disposed on the first surface (111) of the substrate (110);
      ii) a first pair of electrodes (120a, 120b) disposed between the first surface (111) of the substrate (110) and the first absorbable material layer (130); and
      iii) an insulating film (140) disposed on a first surface (131) of the first absorbable material layer (130);
      wherein incontinence is detected on the first incontinence detection cell (100) when the first pair of electrodes (120a, 120b) is bridged by a connecting material;

wherein when the first absorbable material layer (130) is dry, an open circuit is formed between the first pair of electrodes (120a, 120b), wherein when the first absorbable material layer (130) is wetted, the connecting material comprises the wet first absorbable material layer (130), thus operably connecting the first pair of electrodes (120a, 120b) and forming the closed circuit between the pair of electrodes (120a, 120b) for detecting incontinence; and c) a second incontinence detection cell (100) comprising a second pair of electrodes (120a, 120b) disposed on the first surface (111) of the substrate (110);

wherein incontinence is detected on the second incontinence detection cell (100) when the second pair of electrodes (120a, 120b) is bridged by a connecting material, wherein the connecting material comprises a semi solid object, wherein when the connecting material is absent, an open circuit is formed between the second pair of electrodes (120a, 120b), wherein when the connecting material is present and bridges the second pair of electrodes (120a, 120b), a closed circuit is formed between the second pair of electrodes (120a, 120b) and incontinence is detected.

2. The system of claim 1, further comprising a controller comprising a memory, a processor operably coupled to the memory and the electrodes, and a transmitter operably coupled to the processor, wherein the memory comprises computer-readable instructions that, when executed by the processor, causes the processor to perform operations comprising detecting signals from the electrodes and transmitting said signals to a server via the transmitter.

3. The system of claim 1, wherein the insulating film (140) further comprises at least one gap (145) within the insulating film (140); wherein the gap (145) is configured to allow a liquid to reach the first absorbable material layer (130).

4. An incontinence detection cell (100) comprising:
a) a substrate (110) comprising a first surface (111);
b) a first absorbable material layer (130) disposed on the first surface (111) of the substrate (110); wherein the first absorbable material layer (130) is disposed directly on a surface (121) of the electrodes
c) at least one pair of electrodes (120a, 120b) disposed between the first surface (111) of the substrate (110) and the first absorbable material layer (130), and
d) an insulating film (140) disposed on a first surface (131) of the first absorbable material layer (130);
wherein incontinence is detected when the pair of electrodes (120a, 120b) is bridged by a connecting material, the pair of electrodes (120a, 120b) become operably connected, and a closed circuit is formed.

5. An incontinence detection cell (100), comprising:
a) a substrate (110) comprising a first surface (111);
b) a first absorbable material layer (130) disposed on the first surface (111) of the substrate (110); wherein the first absorbable material layer (130) is disposed directly on a surface (121) of the electrodes
c) at least one pair of electrodes (120a, 120b) disposed between the first surface (111) of the substrate (110) and the first absorbable material layer (130), and
d) an insulating film (140) comprising at least one gap (145) disposed on a first surface (131) of the first absorbable material layer (130); wherein the gap (145) is configured to allow a liquid to reach the first absorbable material layer (130):
wherein incontinence is detected when the pair of electrodes (120a, 120b) is bridged by a connecting material, the pair of electrodes (120a, 120b) become operably connected, and a closed circuit is formed.

\* \* \* \* \*